(12) United States Patent
Lanteri et al.

(10) Patent No.: US 11,731,165 B2
(45) Date of Patent: Aug. 22, 2023

(54) STRESSED-SKIN BACKING PANEL FOR IMAGE ARTIFACTS PREVENTION

(71) Applicant: GE Precision Healthcare LLC, Milwaukee, WI (US)

(72) Inventors: Frederic Lanteri, Le Cannet (FR); Edouard Da Cruz, Nice (FR); Flavien Daloz, Biot (FR); Coraly Cuminatto, Le Cannet (FR); Douglas Glenn Wildes, Clifton Park, NY (US)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 727 days.

(21) Appl. No.: 16/722,359

(22) Filed: Dec. 20, 2019

(65) Prior Publication Data
US 2021/0187549 A1 Jun. 24, 2021

(51) Int. Cl.
*B06B 1/06* (2006.01)
*A61B 8/00* (2006.01)
*H10N 30/80* (2023.01)

(52) U.S. Cl.
CPC ............ *B06B 1/067* (2013.01); *A61B 8/4444* (2013.01); *A61B 8/546* (2013.01); *B06B 1/0685* (2013.01); *H10N 30/80* (2023.02)

(58) Field of Classification Search
CPC ........ B06B 1/067; B06B 1/0685; H01L 41/04
See application file for complete search history.

(56) References Cited

U.S. PATENT DOCUMENTS

| | | | |
|---|---|---|---|
| 5,267,221 A | 11/1993 | Miller | |
| 2004/0100163 A1* | 5/2004 | Baumgartner | B06B 1/0622 310/334 |
| 2013/0315035 A1* | 11/2013 | Tai | A61B 8/4494 367/140 |
| 2015/0115773 A1* | 4/2015 | Li | A61B 8/12 29/25.35 |
| 2018/0175278 A1* | 6/2018 | Daloz | A61B 8/4483 |

FOREIGN PATENT DOCUMENTS

WO 2018065400 A1 4/2018

OTHER PUBLICATIONS

PCT application PCT/US2020/064844 filed Dec. 14, 2020—International Search Report/Written Opinion dated Apr. 7, 2021, 14 pages.

* cited by examiner

*Primary Examiner* — Bryan P Gordon
(74) *Attorney, Agent, or Firm* — McAndrews, Held & Malloy, Ltd.; Jacob Groethe; David Bates

(57) ABSTRACT

A backing panel for a transducer of an ultrasound scanner probe, comprising a core layer sandwiched by a first skin layer and a second skin layer. The transducer may comprise a front portion and a rear portion, where the front portion points to a direction of a target for the ultrasound scanner probe, and the first skin layer is adjacent to the rear portion of the transducer.

20 Claims, 12 Drawing Sheets

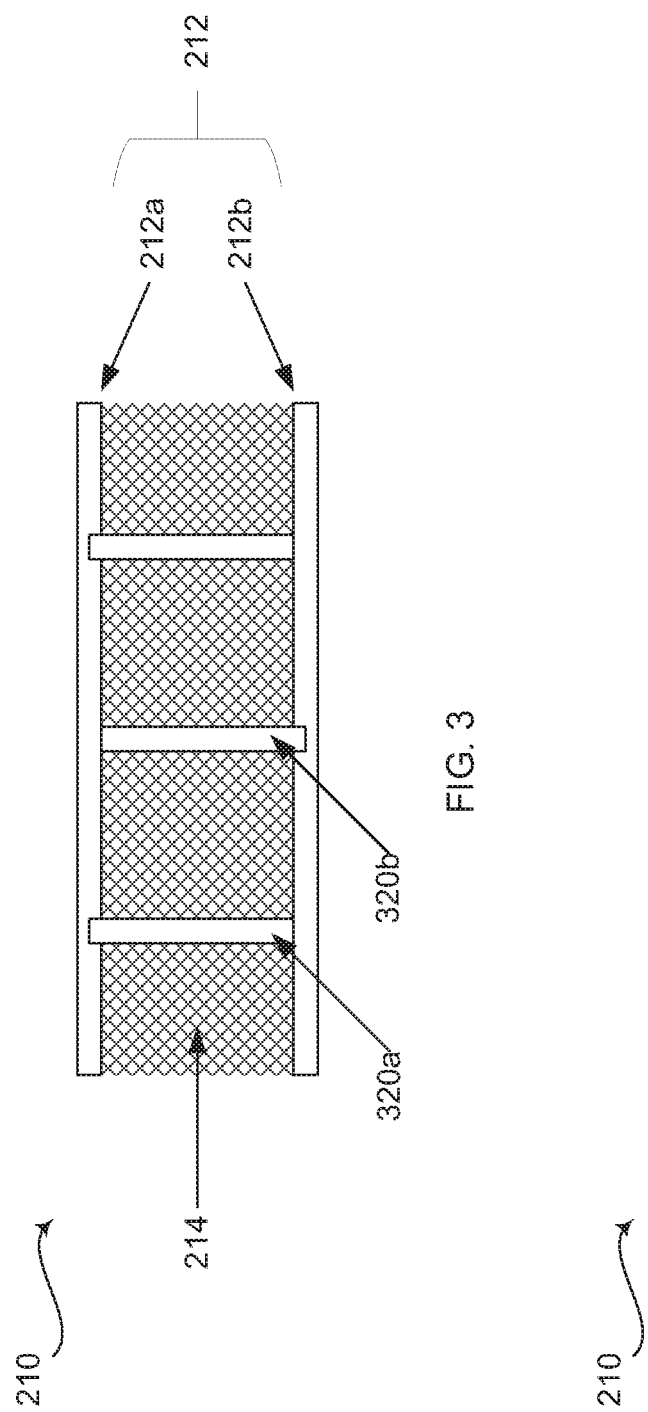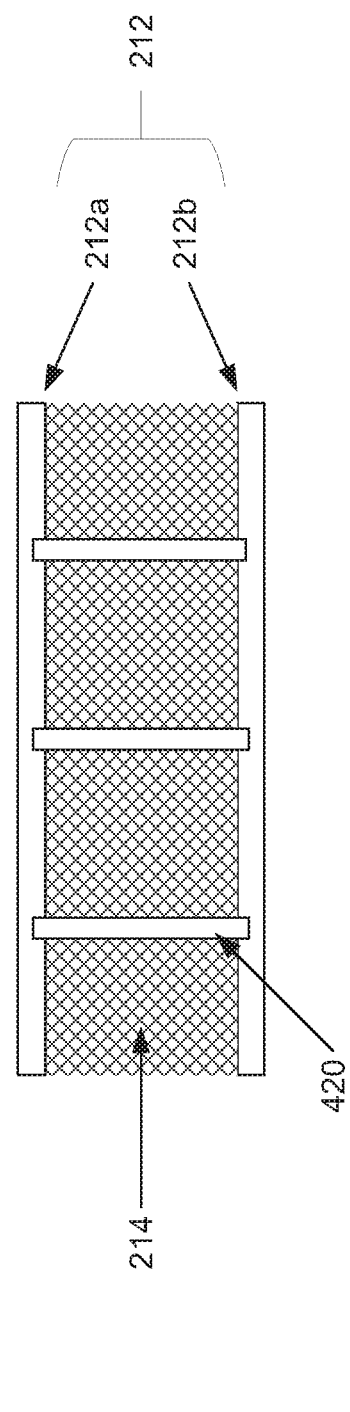
FIG. 3
FIG. 4

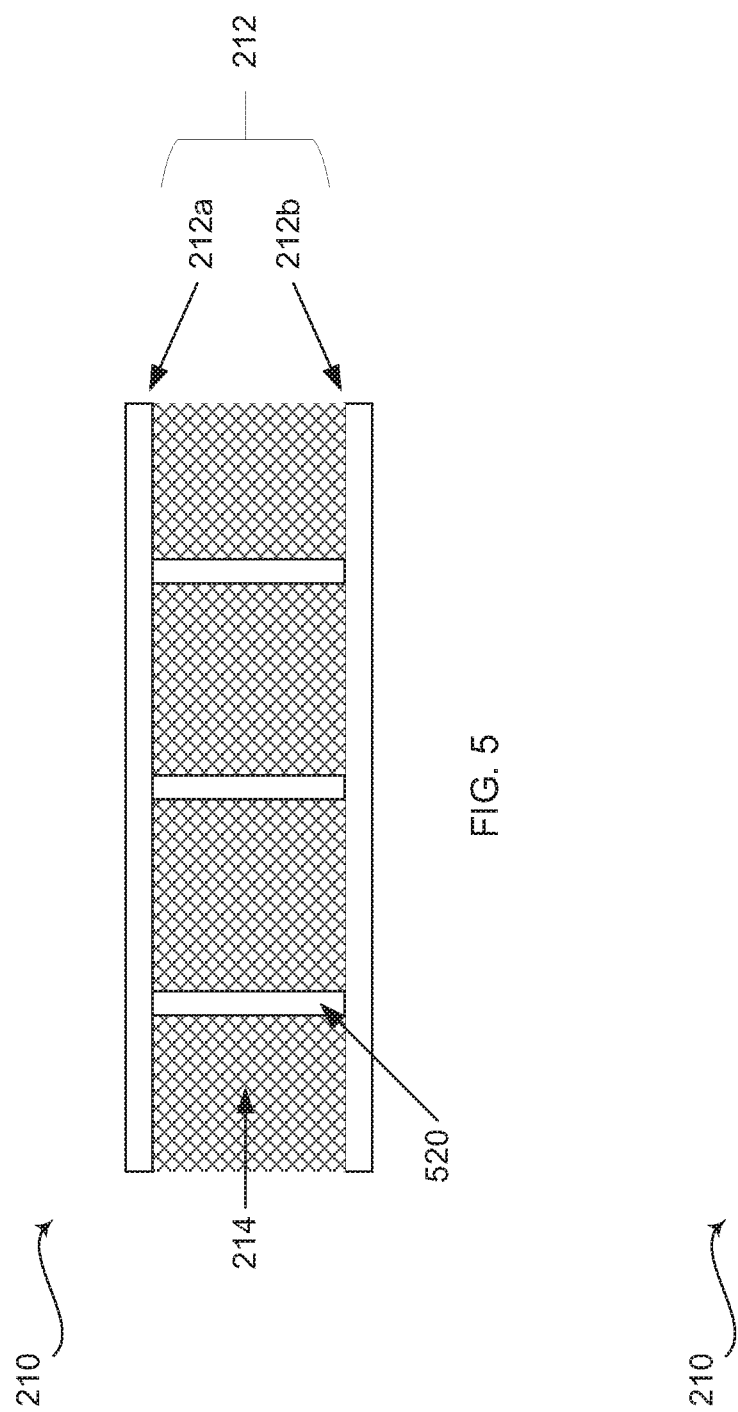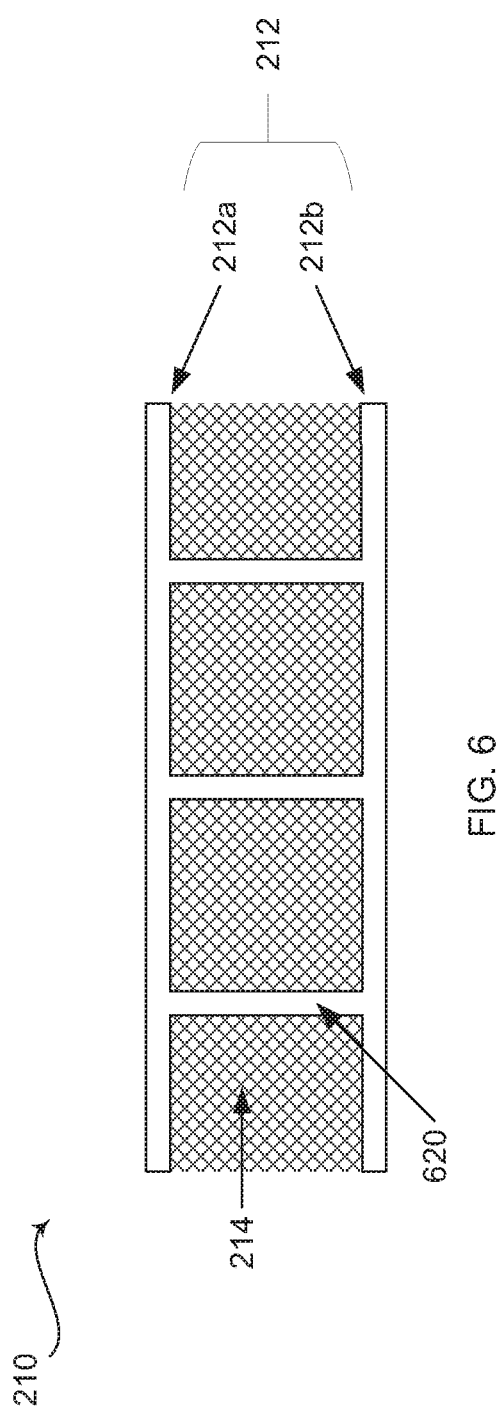

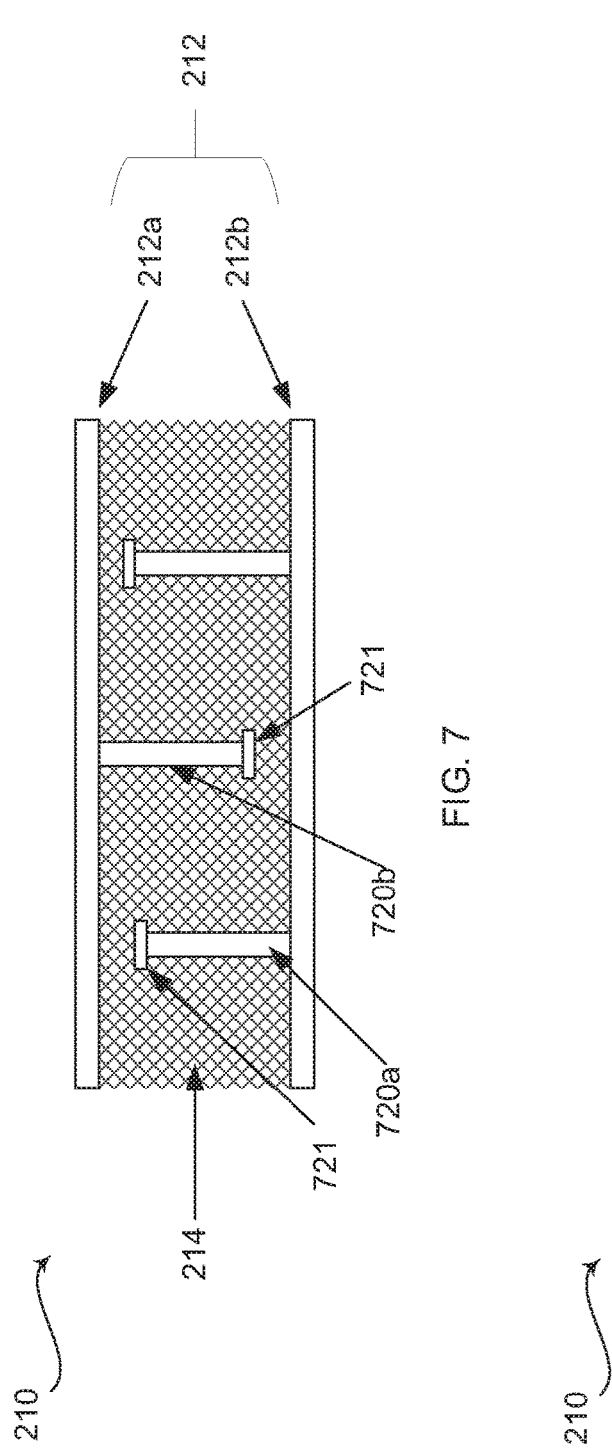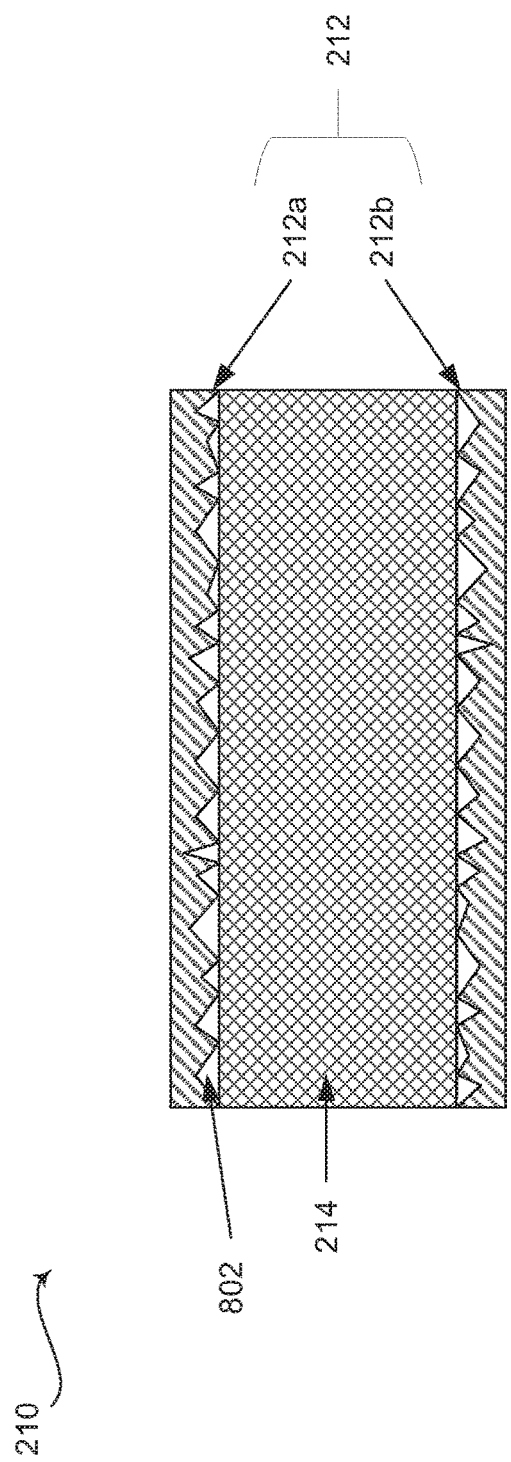

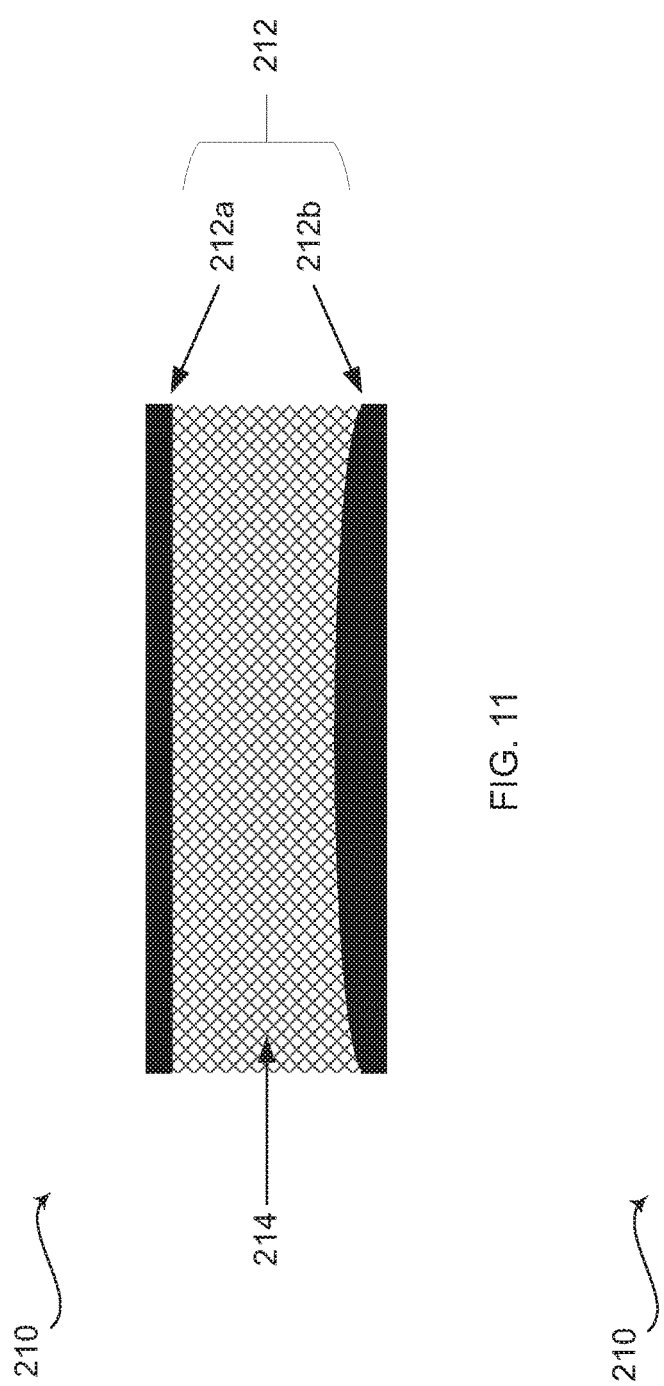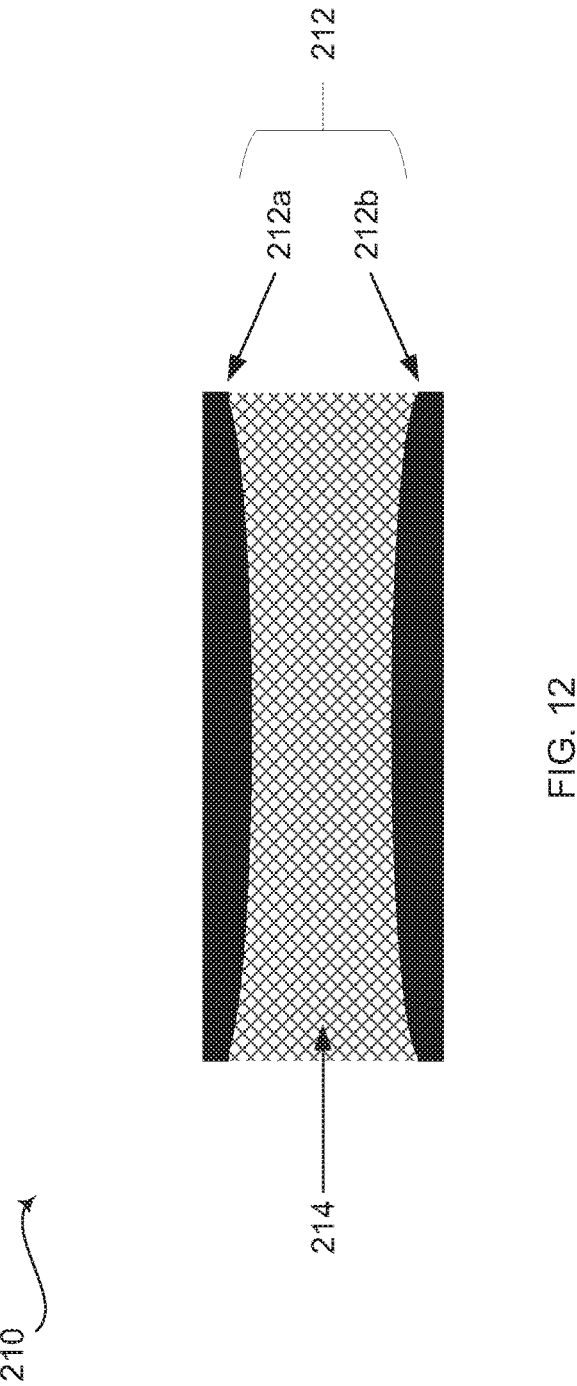

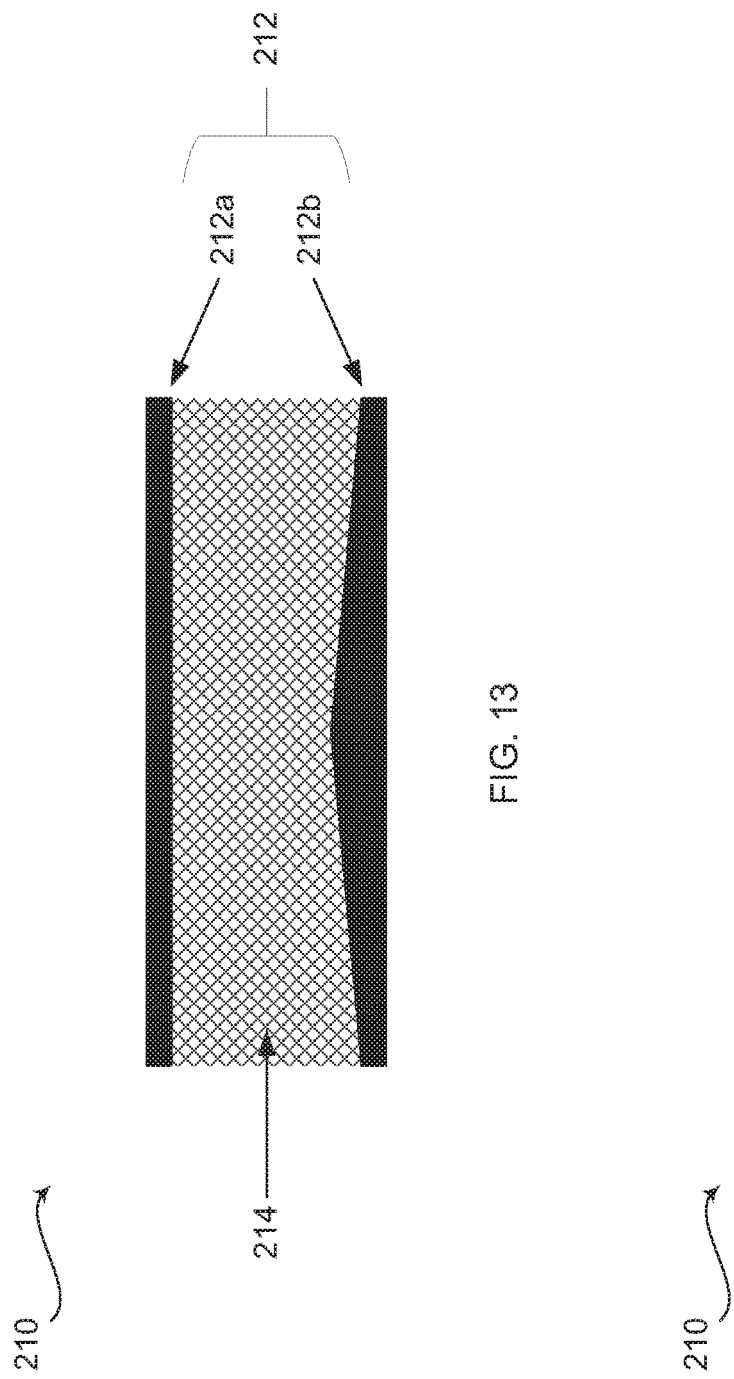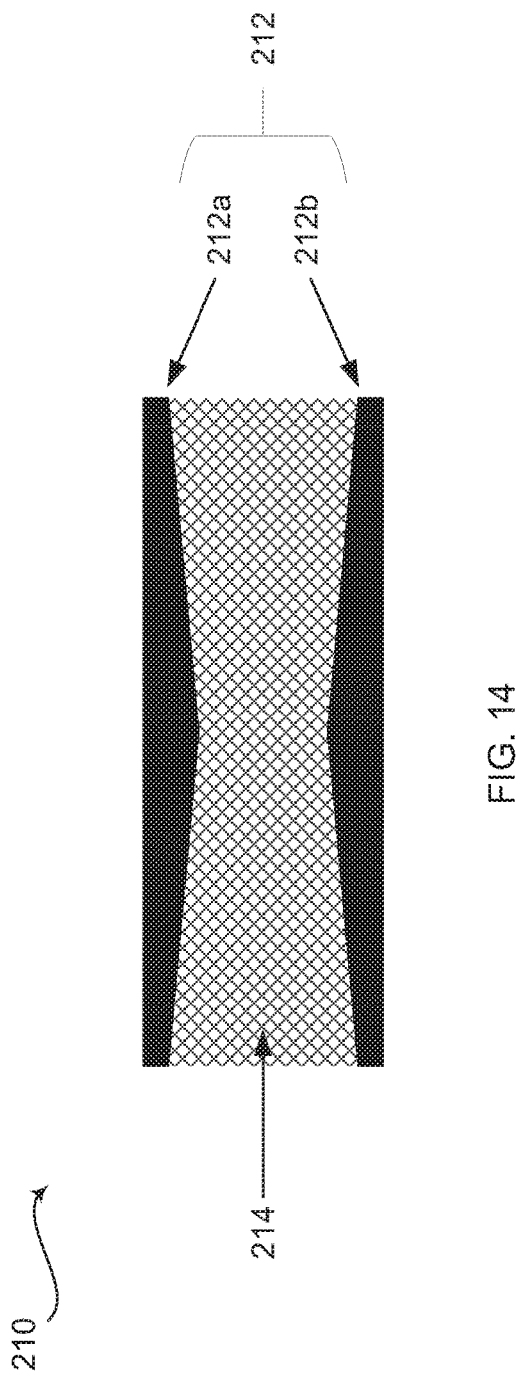

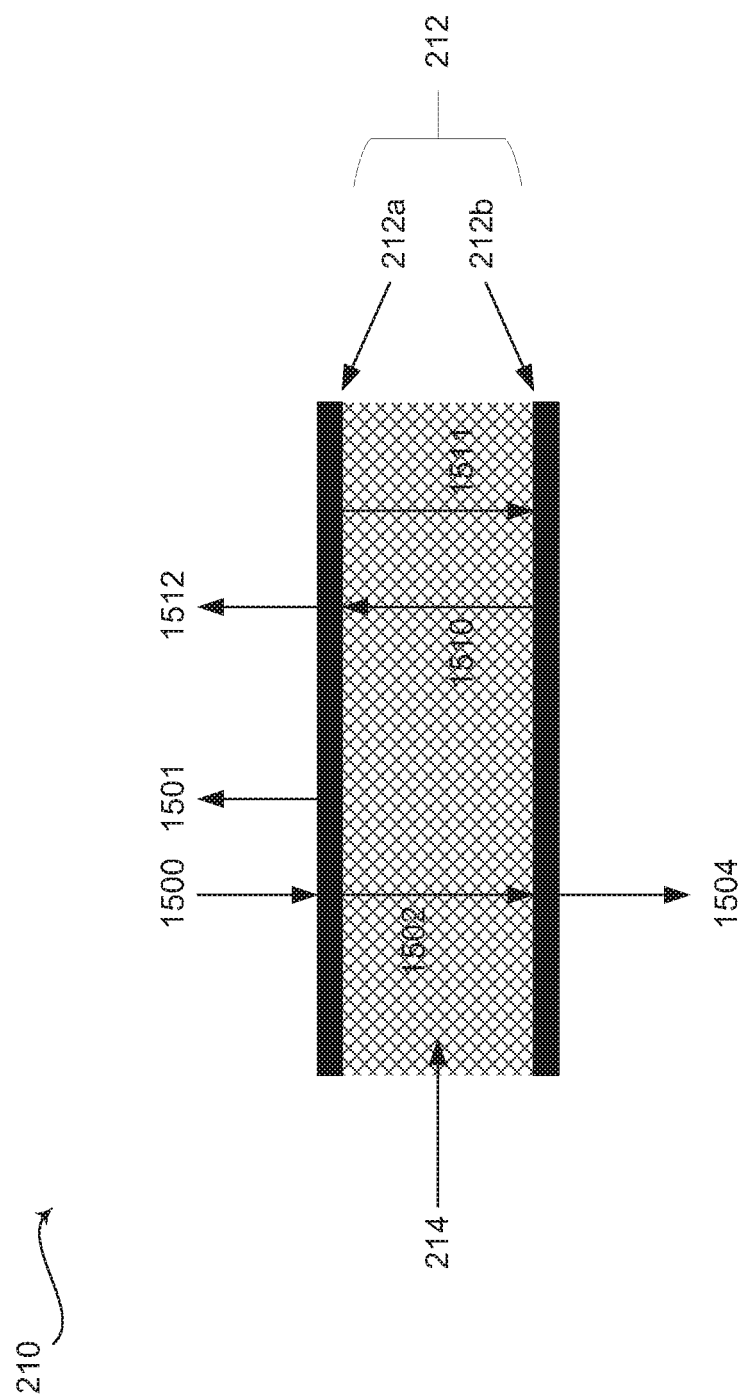

STRESSED-SKIN BACKING PANEL FOR IMAGE ARTIFACTS PREVENTION

FIELD

Certain embodiments relate to an acoustic structure. More specifically, certain embodiments relate to stressed-skin backing panel for image artifacts prevention.

BACKGROUND

Medical imaging machines such as, for example, an ultrasound scanner, may be used for imaging at least a portion of a patient's body as part of diagnostic procedures. The ultrasound scanner may comprise a probe that emits, for example, acoustic waves.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A stressed-skin backing panel for image artifacts prevention, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

BRIEF DESCRIPTION OF SEVERAL VIEWS OF THE DRAWINGS

FIGS. 3-14 are illustrations of exemplary stressed-skin backing panels, in accordance with various embodiments.

FIG. 15 is an illustration of example propagation of acoustic waves, in accordance with various embodiments.

DETAILED DESCRIPTION

Figure 1:
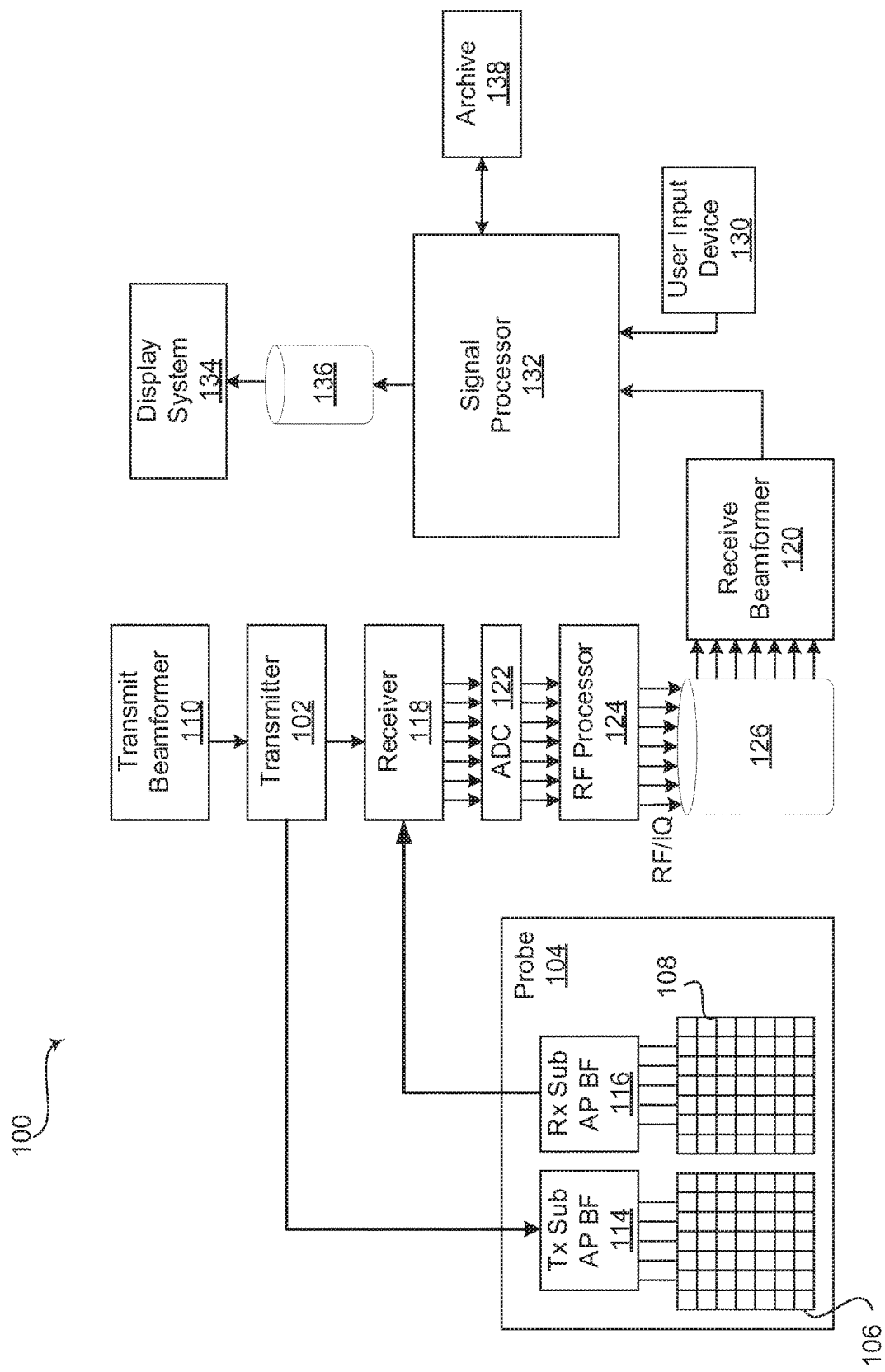
FIG. 1 is a block diagram of an exemplary ultrasound system, in accordance with various embodiments.

Certain embodiments may be found in a method and system for stressed-skin backing panel for image artifacts prevention. Image artifacts root cause may depend on the application. In some situations, image artifacts can be caused by echoes reflected at some interface in the rear structure of the transducer that cannot be filtered by the imaging system and combine with the signal of interest from the observed region of the human body. In some other situations such as intracardiac application, image artifacts may happen when the acoustic waves propagate through the entire transducer structure and may insonify human body structures outside of the region of interest. For example, in various embodiments, the acoustic structure of ultrasound transducers may include an absorbing layer (backing) intended to absorb energy radiated in the direction opposite to the observation direction in order to minimize spurious back echoes that would combine with useful signals sent and cause image artifacts. In some embodiments, thinner backing panels with sufficient mechanical stiffness may be useful. As used, the term stressed-skin panel refers to a type of rigid construction that comprises an inner core sandwiched between two skins.

A thin absorbing backing may be used, for example, where space is at a premium. The absorbing backing may also provide sufficient mechanical stiffness conducive for fabrication purposes. The absorbing backing may also remove heat to prevent front temperature from exceeding a maximum temperature allowed by appropriate regulations.

The foregoing summary, as well as the following detailed description of certain embodiments will be better understood when read in conjunction with the appended drawings. The figures provided illustrate diagrams of the functional blocks of various embodiments, and the functional blocks are not necessarily indicative of the division between mechanical parts.

It should be understood that the various embodiments are not limited to the arrangements and instrumentality shown in the drawings, and that various embodiments may be combined. Other embodiments may be utilized and structural changes may be made without departing from the scope of the various embodiments. For example, different types of materials with similar mechanical properties may be used in various embodiments of the disclosure. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also, as used herein, the term "imaging machine" broadly refers to an ultrasound scanner. However, other devices and/or structures that need to absorb sound energy may also use an embodiment of the disclosure.

Various embodiments of the disclosure may provide for a backing structure that consists of a "core" layer sandwiched between two "skin" layers. The material that forms the core layer may be made of a highly attenuating or diffusing material such as, for example, but not limited to, epoxy matrix filled with attenuating and diffusing particles such as for example, but not limited to, tungsten or alumina powder, or silicone based compositions, where the "skin" layers may comprise a stiff material such as, for example, but not limited to, tungsten carbide. The backing structure may be configured such that sound energy (waves) entering the structure may be trapped in the core layer and highly attenuated due to a design for strong reflection at the interface between the "skin" and "core" layers.

For example, when energy enters the backing structure, propagation in the "core" of the backing structure ensures attenuation of this energy. First reflection happens at core/bottom skin layer interface due to strong acoustic impedance mismatch between the core material and skin material. Energy reflected at this interface propagates again in the core layer, is reflected at core/top skin layer interface, and so on to minimize the amplitude of spurious waves that go out of the backing structure. The core material may have low acoustic impedance in the range of, for example, a few MRay. For example, the acoustic impedance may be less than 1 MRay for foam, about 1 MRay for silicone, 4-6 MRay for an epoxy matrix filled with metal particles, etc. The skin material may have higher acoustic impedance in the range of 10s to 100s of MRay. For example, the acoustic impedance may be approximately 80-100 MRay for tungsten carbide.

Various embodiments may also include a structure that comprises a number of stiffeners made from, for example, the same material as the skin layers. The stiffeners may be referred to as "support pillars." Still other embodiments may include support pillars that are made of different material than the skin layers.

In various embodiments, both "skin" and "core" layers may be designed in such a way that the thermal conductivity of the stressed-skin backing structure contributes to drain heat out from the front face of the transducer. The core layer may be, for example, a composite material that comprises one or more of highly conductive metal particles, graphite, etc., where the graphite may comprise one or more of, for example, pyrolitic graphite, graphene, etc.

FIG. 1 is a block diagram of an exemplary ultrasound system 100, in accordance with various embodiments. Referring to FIG. 1, there is shown an ultrasound system 100. The ultrasound system 100 comprises a transmitter 102, an ultrasound probe 104, a transmit beamformer 110, a receiver 118, a receive beamformer 120, A/D converters 122, a RF processor 124, a RF/IQ buffer 126, a user input device 130, a signal processor 132, an image buffer 136, a display system 134, and an archive 138.

The transmitter 102 may comprise suitable logic, circuitry, interfaces and/or code that may be operable to drive an ultrasound probe 104. The ultrasound probe 104 may comprise a two dimensional (2D) array of piezoelectric elements. The ultrasound probe 104 may comprise a group of transmit transducer elements 106 and a group of receive transducer elements 108, that normally constitute the same elements. In certain embodiment, the ultrasound probe 104 may be operable to acquire ultrasound image data covering at least a substantial portion of an anatomy, such as the heart, a blood vessel, or any suitable anatomical structure.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input device 130 may be utilized to input patient data, scan parameters, settings, select protocols and/or templates, and the like. In an exemplary embodiment, the user input device 130 may be operable to configure, manage and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include button(s), rotary encoder(s), a touchscreen, motion tracking, voice recognition, a mouse device, keyboard, camera and/or any other device capable of receiving a user directive. In certain embodiments, one or more of the user input devices 130 may be integrated into other components, such as the display system 134 or the ultrasound probe 104, for example. As an example, user input device 130 may include a touchscreen display.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information.

The signal processor 132 may be one or more central processing units, microprocessors, microcontrollers, and/or the like. The signal processor 132 may be an integrated component, or may be distributed across various locations, for example. In an exemplary embodiment, the signal processor 132 may be capable of receiving input information from a user input device 130 and/or archive 138, generating an output displayable by a display system 134, and manipulating the output in response to input information from a user input device 130, among other things. The signal processor 132 may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

Figure 2:
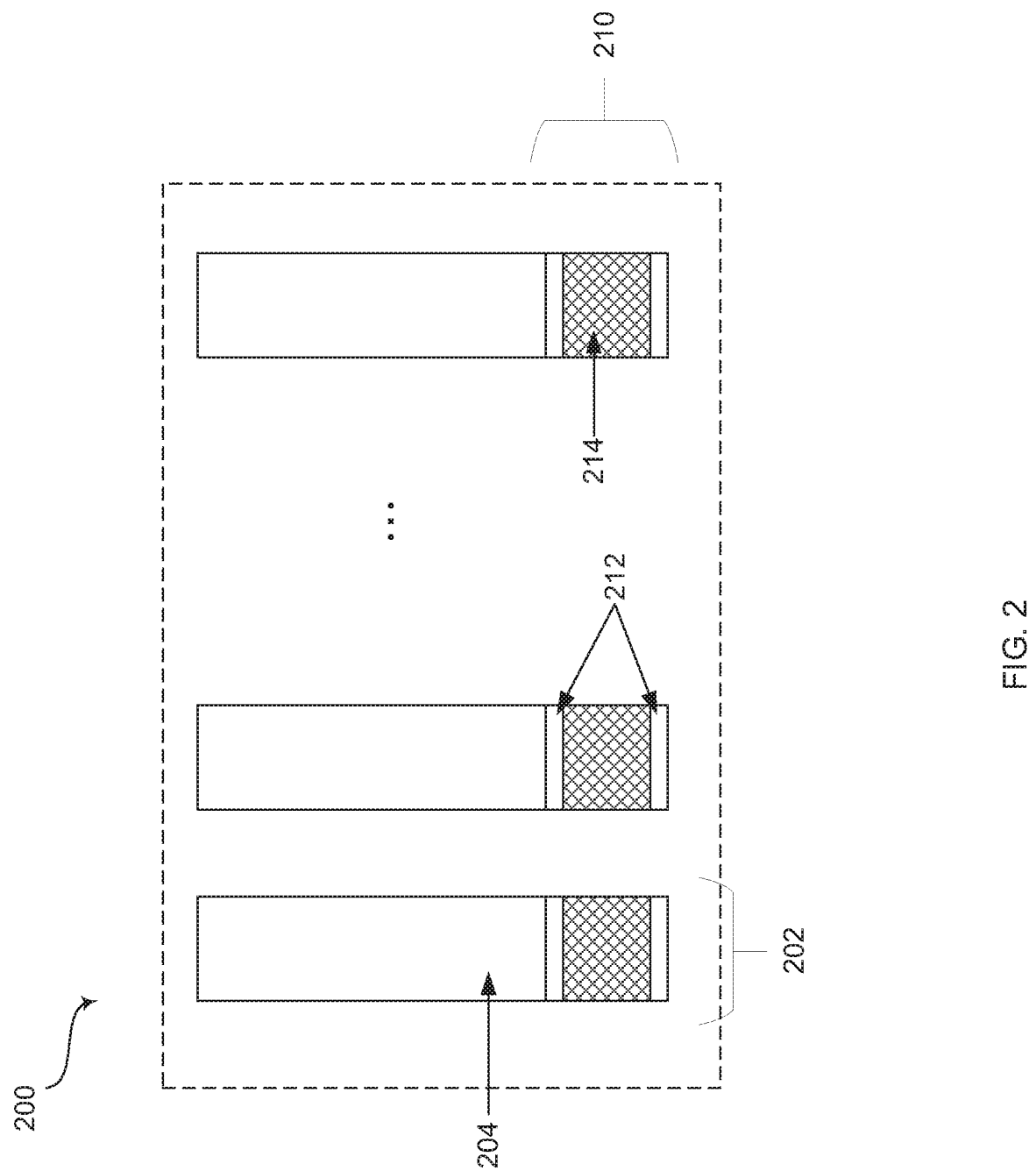
FIG. 2 is an illustration of a portion of an exemplary probe for an ultrasound system, in accordance with various embodiments.

FIG. 2 is an illustration of a portion of an exemplary probe for an ultrasound system, in accordance with various embodiments. Referring to FIG. 2, there is shown a probe 200 with transducer elements 202. The transducer elements 202 may be similar to, for example, the transmit transducer elements 106 and/or the receive transducer elements 108. Each transducer element 202 may comprise, for example, the transducer 204 and a stressed-skin backing panel 210. The stressed-skin backing panel 210 may comprise, for example, a first and a second skin layers 212 sandwiching a core layer 214.

The transducer 204 may be any suitable transducer made from material such as, for example, lead zirconate titanate (PZT), single crystal piezoelectric elements, etc., or transducer types such as, for example, capacitive micromachined ultrasonic transducer (CMUT), etc.

The stressed-skin backing panel 210 may provide an acoustically efficient absorbing structure. The level of absorption provided by the stressed-skin backing panel 210 may depend on, for example, the transducer design and the targeted application. The stressed-skin backing panel 210 may, for example, provide that the amplitude of the echo reflected at the bottom face of the stressed-skin backing panel 210 is approximately 60 dB lower (or more than 60 dB lower) than the amplitude of the main echo received in a test setup. For example, the test setup may include a transducer piezoelectric element that is excited so that the transducer radiates acoustic waves in water in front of a perfectly reflecting target. In the same way, for example for a catheter application, the stressed-skin backing panel 210 may provide that the rejection level between waves echoed from the front side (region of interest of human body) and waves echoes from the region in the opposite direction is better than, for example, 60 dB. Accordingly, the stressed-skin backing panel 210 may be used for a variety of applications, including applications where there are thickness footprint and backing stiffness constraints. These applications may include, for example, transducers mounted in a catheter for intracardiac applications.

The transducer 204 may comprise, for example, at least one active layer (PZT, single crystal, etc.) and a set of matching layers. The total thickness of this sub-system may be, for example, a few hundred microns, where the thickness may be driven by a frequency at which the transducer operates and by the material used. Degrees of freedom to significantly reduce this sub-system thickness may be limited. The thickness of layers for a device (e.g., ASIC) incorporated in the stack to electrically drive the transducer may also be somewhat limited by technology, and may be in the range of a few hundred microns. Accordingly, the space that can be used for the backing may be limited to some hundreds of microns.

In various embodiments of the disclosure, the core layer 214 may comprise, for example, polymer based material such as silicone or epoxy, carbon or polymer based foam, one or more graphites such as, for example, pyrolitic graphite, graphene, etc. The first and second skin layers 212 may comprise material that may provide stiffness to the stressed-skin backing panel 210 such as, for example, tungsten carbide, brass, steel, silicon carbide, etc.

A percentage of the sound energy incident to the stressed-skin backing panel 210 may enter the stressed-skin backing panel 210 into the core layer 214, and then the sound energy may be trapped in the core layer 214. The sound energy may be trapped in the core layer 214 due to reflection of a percentage of the sound energy at the core layer 214 and the skin layers 212. For example, a percentage of the sound energy in the core layer 214 that reflects off the skin layers 212 may be larger than a percentage of sound energy incident to the stressed-skin backing panel 210 that reflects off the skin layer 212. A percentage of the sound energy in the core layer 214 that is reflected off the skin layer 212 may be given by Equation 1 for the reflection coefficient R at the interface between the "core" material and the "skin" material:

$$R = (Zskin - Zcore)/(Zskin + Zcore) \qquad \text{Equation 1}$$

where "Zskin" is the acoustic impedance of the "skin" material and "Zcore" is the acoustic impedance of the "core" material. may be about 80 MRay. As an example, when Zskin=4 MRay and Zcore=80 MRay, the reflection coefficient R is greater than 0.9. That is, the energy that is reflected is greater than 90% of the incident energy.

FIGS. 3-14 are illustrations of exemplary stressed-skin backing panels, in accordance with various embodiments. Referring to FIG. 3, there is shown the stressed-skin backing panel 210 with the skin layers 212 and the core layer 214. There is also shown support pillars 320a and 320b. As shown, the support pillar 320a may be flush against the lower skin layer 212b and embedded in the upper skin layer 212a. The support pillar 320b may be flush against the upper skin layer 212*a* and embedded in the lower skin layer 212*b*. A lower end of the support pillar 320*a* may be attached to the lower skin layer 212*b* or butted against the lower skin layer 212*b*. Similarly, an upper end of the support pillar 320*b* may be attached to the upper skin layer 212*a* or butted against the upper skin layer 212*a*. Accordingly, the support pillars 320*a*, 320*b* may alternate in being embedded into the upper skin layer 212*a* or the lower skin layer 212*b* to provide stiffness support for the stressed-skin backing panel 210.

Referring to FIG. 4, there is shown the stressed-skin backing panel 210 with the skin layers 212, the core layer 214, and support pillars 420. As shown, each of the support pillars 420 may be embedded in the upper and lower skin layers 212. Accordingly, the support pillars 420 embedded in the skin layers 212 may provide stiffness support for the stressed-skin backing panel 210.

Referring to FIG. 5, there is shown the stressed-skin backing panel 210 with the skin layers 212, the core layer 214, and support pillars 520. As shown, each of the support pillars 520 may be flush with the upper and lower skin layers 212. The ends of the support pillars 520 may be attached to the skin layers 212 or butted against the skin layers 212. Accordingly, the support pillars 420 may provide stiffness support for the stressed-skin backing panel 210.

Referring to FIG. 6, there is shown the stressed-skin backing panel 210 with the skin layers 212, the core layer 214, and support pillars 620. As shown, the support pillars 620 and the upper and lower skin layers 212 may be a unitary piece that may have been, for example, formed together as a single unit. Accordingly, the support pillars 620 may provide stiffness support for the stressed-skin backing panel 210.

Referring to FIG. 7, there is shown the stressed-skin backing panel 210 with the skin layers 212, the core layer 214, and support pillars 720*a* and 720*b*. As shown, the support pillars 720*a* may be flush with the lower skin layer 212 and the support pillars 720*b* may be flush with the upper skin layer 212. Accordingly, the support pillars 720*a* and 720*b* may provide stiffness support for the stressed-skin backing panel 210. Additionally, various embodiments of the disclosure may have the support pillars 720*a* embedded in the lower skin layer 212*b* and the support pillars 720*b* embedded in the upper skin layer 212*a* similarly as in FIG. 3. Furthermore, in some embodiments, the ends of the support pillars 720*a* and 720*b* that are in the core layer 214 may be enlarged to form a foot 721 that may help anchor the support pillars 720*a* and 720*b* in the core layer 214. The ends of the support pillars 720*a* and 720*b* may be attached to the respective skin layer 212 or butted against the respective skin layer 212. Accordingly, the support pillars 720*a* and 720*b* may provide stiffness support for the stressed-skin backing panel 210.

Various embodiments of the disclosure may have support pillars that are of different shapes. For example, a horizontal cross-section of the support pillar may be round, elliptical, rectangular, etc. Accordingly, a support pillar may also be extended in a direction perpendicular to the drawings (direction extending into/out of the sheets of paper of the drawings).

Referring to FIG. 8, there is shown the stressed-skin backing panel 210 with the skin layers 212 and the core layer 214. As shown, the surface of the skin layer 212 that faces the core layer 214 may be a non-planar surface. Accordingly, there may be a gap between the skin layer 212 and the core layer 214. The gap may be filled with, for example, one or more epoxy material 802 to have the skin layers 212 adhere to the core layer 214. While the epoxy material 802 may be different than the material for the skin layers 212 or the core layer 214, various embodiments of the disclosure may have the epoxy material 802 be the same as the material for the core layer 214. For example, this may be the case when the core layer 214 comprises epoxy material or some other material that allows adhesion to the skin layers 212.

Figure 9:
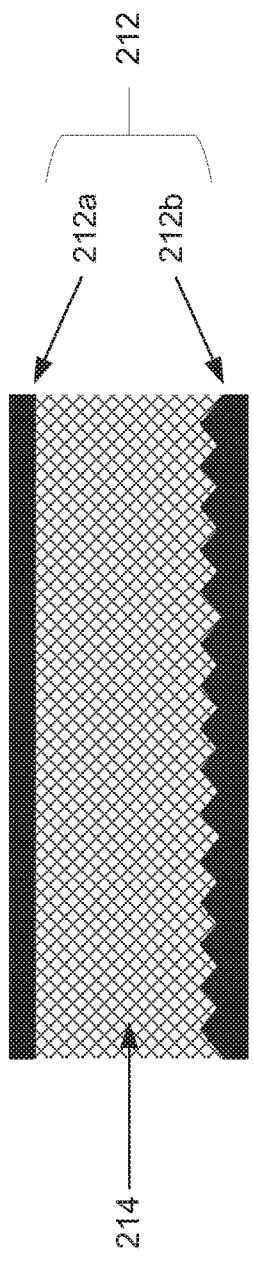
Figure 10:
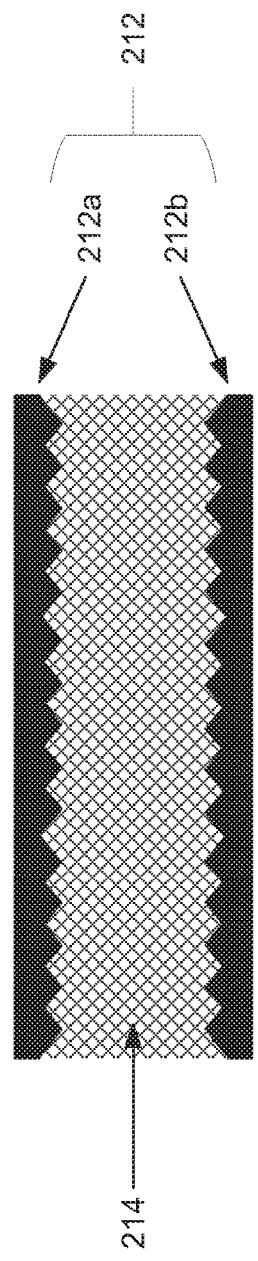

Referring to FIG. 9, there is shown the stressed-skin backing panel 210 with the lower skin layer 212*b* that has a saw-toothed surface similar to the skin layers 212 in FIG. 8. Referring to FIG. 10, there is shown the stressed-skin backing panel 210 with the skin layers 212*a* and 212*b* that both have saw-toothed surfaces similar to the skin layers 212 in FIG. 8.

Referring to FIG. 11, there is shown the stressed-skin backing panel 210 with the lower skin layer 212*b* that has a rounded surface. Referring to FIG. 12, there is shown the stressed-skin backing panel 210 with the skin layers 212*a* and 212*b* that have rounded surfaces.

Referring to FIG. 13, there is shown the stressed-skin backing panel 210 with the lower skin layer 212*b* that has triangular surface. Referring to FIG. 14, there is shown the stressed-skin backing panel 210 with the skin layers 212*a* and 212*b* that have triangular surfaces.

Accordingly, it can be seen that the non-planar surfaces described with respect to FIGS. 8-14 may be used for any embodiment of the present disclosure. Also, while various specific examples were presented, it should be understood that any other non-planar surface may be used for a skin layer. Also, the separate epoxy layer 802 may also be used for any stressed-skin backing panel and/or the core layer 214 for any stressed-skin backing panel may comprise epoxy material. Additionally, it should be understood that any stressed-skin backing panel may comprise any of the support pillars described with respect to FIGS. 3-7, as well as any other support pillars that may provide similar structure.

Various embodiments of the disclosure may reduce interference between multiple echoes in the core layer 214 due to narrow band resonance, which may cause spurious waveform(s) in a transducer impulse response that creates image artifacts. Accordingly, in various embodiments of the disclosure, one or both of the skin layers 212*a* and 212*b* may have a rough profile or grooves, or is shaped (curved, triangular, or any other shape) so that energy may be spread in multiple directions instead of recombining in phase with the incident wave.

FIG. 15 is an illustration of example propagation of acoustic waves, in accordance with various embodiments. Referring to FIG. 15, there is shown the stressed-skin backing panel 210 comprising the core layer 214 sandwiched between the skin layers 212. There is shown an incident acoustic wave 1500 from, for example, the transducer 204. The incident acoustic wave 1500 is transmitted in an undesired direction. Upon reaching the upper skin layer 212*a*, a portion of the incident acoustic wave 1500 is reflected as a reflected acoustic wave 1501, and a portion of the incident acoustic wave travels to the core layer 214 as the acoustic wave 1502.

Upon reaching the lower skin layer 212*b*, a portion of the acoustic wave 1502 is reflected as the acoustic wave 1510, and the a portion of the acoustic wave 1502 is transmitted out of the stressed-skin backing panel 210 as acoustic wave 1504.

Upon reaching the upper skin layer 212*a*, a portion of the acoustic wave 1510 is reflected as acoustic wave 1511 and a portion of the acoustic wave 1510 is transmitted out of the stressed-skin backing panel 210 as acoustic wave 1512. The reflection/transmission of the acoustic wave 1511 may continue similarly as the acoustic wave 1502.

Accordingly, it can be seen that reducing the acoustic waves 1501, 1512, etc., may reduce image artifacts.

Figure 16:
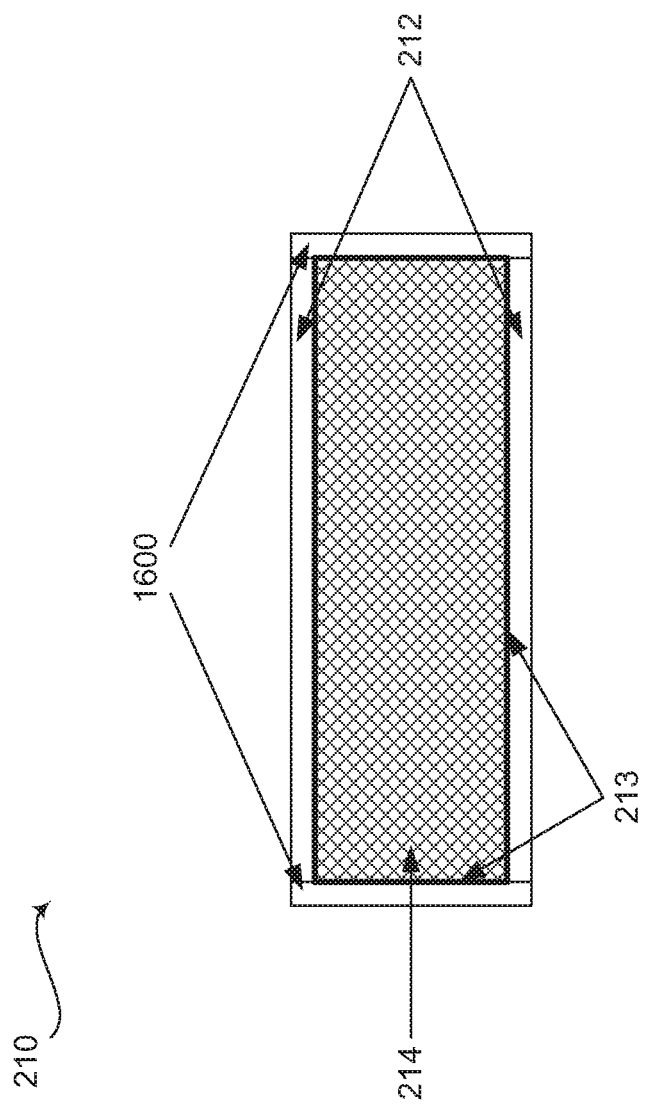
FIG. 16 is an illustration of an example stressed-skin backing panel with skins covering additional surfaces, in accordance with various embodiments.

In the various embodiments of the disclosure, there have been shown a vertical cross-section of a stressed-skin backing panel 210 with an upper and lower skin layers 212. However, various embodiments of the disclosure may also comprise other skin layers that cover one or more of the other peripheral surfaces of the stressed-skin backing panel 210. For example, FIG. 16 illustrates the side surfaces of the stressed-skin backing panel 210 covered by skin layers 1600. Similarly, the front and rear surfaces of the stressed-skin backing panel 210 may also be covered by a respective skin layer. Various embodiments of the disclosure may have all skin layers (212, 1600, etc.) be similar as described with respect to FIGS. 2-14, or different skin layers may have different properties (for example, reflection property for sound energy). As described earlier, there may be an epoxy layer 213 between the skin layers 212 and/or 1600 and the core layer 214.

Figure 17:
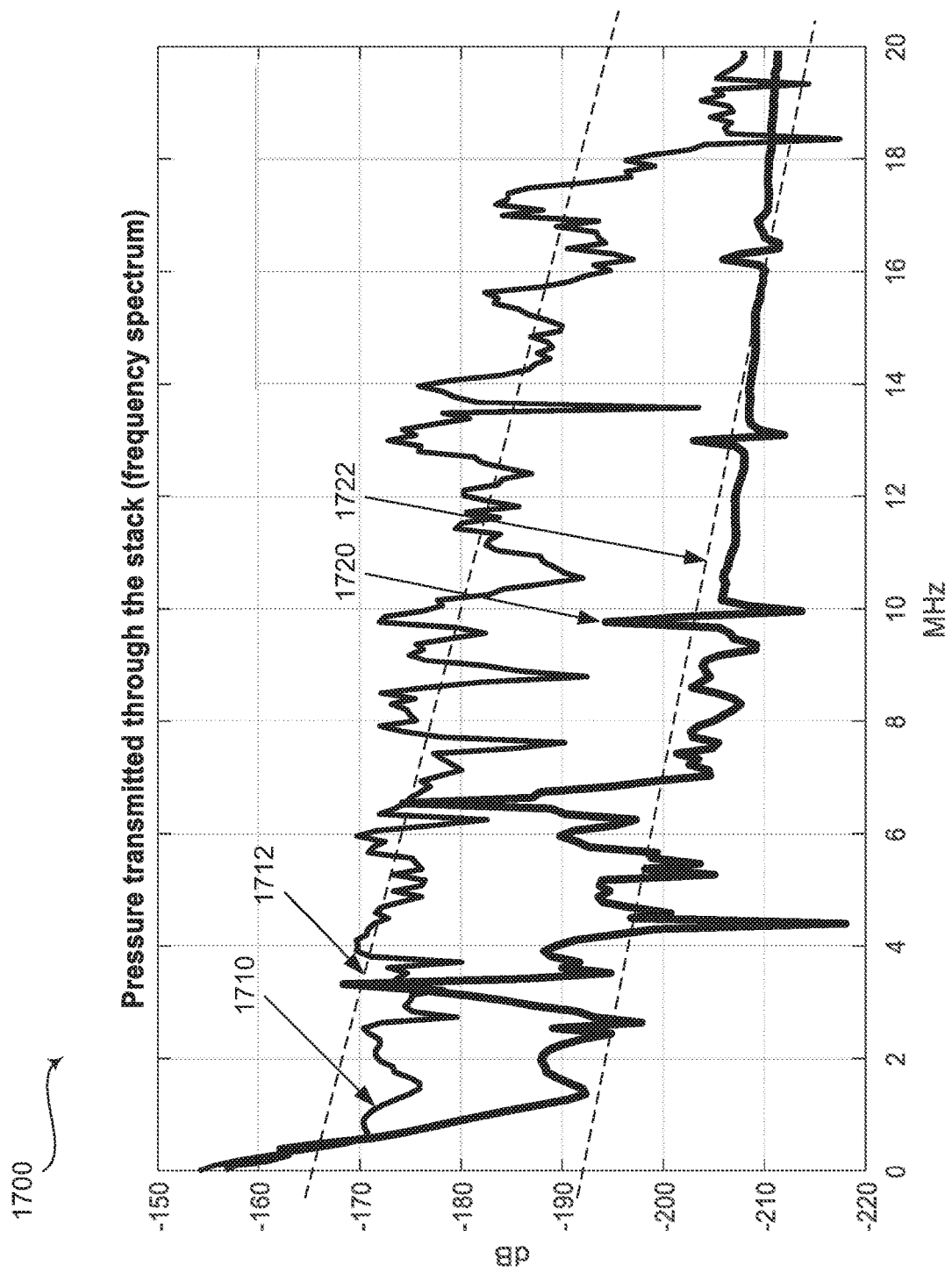
FIG. 17 is an illustration of a graph of a finite element simulation of an example embodiment stressed skin backing panel.

FIG. 17 is an illustration of a graph of a finite element simulation of an example embodiment. Referring to FIG. 17, there is shown an illustration of a graph 1700 with sound frequency along the X-axis and sound level (pressure) in the Y-axis. The graph 1700 represents sound pressure transmitted through a transducer element 202 as a function of frequency when the transducer element 202 receives an acoustic wave.

There is shown a graph 1710 for a conventional backing panel and a graph 1720 for an embodiment of a stressed-skin backing panel. There are shown interpolated linear graphs 1712 for the graph 1710 and interpolated linear graph 1722 for the graph 1720. As can be seen from the interpolated graphs 1712 and 1722, the stressed-skin backing panel provides approximately 20 dB better back/front rejection than a conventional backing panel.

Figure 18:
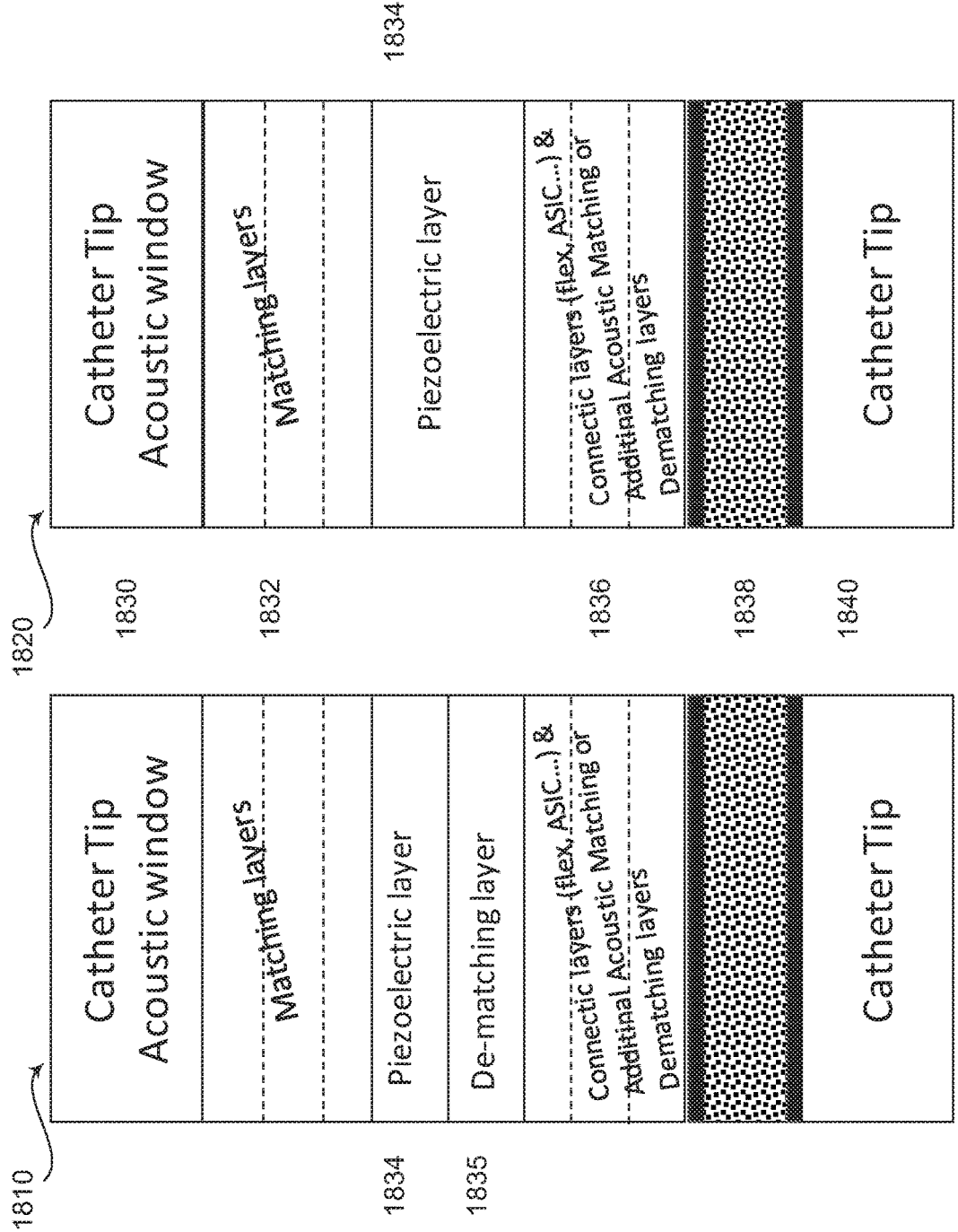
FIG. 18 illustrates example transducer structures for catheter applications, in accordance with various embodiments.

FIG. 18 illustrates example transducer structures for catheter applications, in accordance with various embodiments. Referring to FIG. 18, there are shown transducer structures 1810 and 1820. The transducer structure 1810 comprises a catheter tip acoustic window 1830, matching layers 1832, piezoelectric layer 1834, a de-matching layer 1835, a connectic layer 1836, the stressed-skin backing panel 1838 similar to the stressed-skin backing panel 210, and a catheter tip 1840.

Acoustic waves may be generated by transmit transducers in the piezoelectric layer 1834 to be transmitted through the catheter tip acoustic window 1830. The transmit transducers may be similar to, for example, the transmit transducer elements 106.

The matching layers 1832 may be designed to maximize transmission of the acoustic waves generated in the piezoelectric layer 1834 toward a target to be scanned. The de-matching layer 1835 may be designed to maximize reflection of the acoustic waves transmitted toward the catheter tip 1840. Due to the short amount of propagation delay before the acoustic wave reflected from the de-matching layer 1835 is received by a receiving transducer, the acoustic wave from the de-matching layer 1835 may be filtered out by a receive gate that is turned on after the short propagation delay. The receiving transducer may be similar to, for example, the receive transducer element 108.

Accordingly, less acoustic waves may be transmitted to the stressed-skin backing panel 1838, which is similar to the stressed-skin backing panel 210. Therefore, less acoustic waves may be reflected from the stressed-skin backing panel 1838 to the receiving transducer that may be in the piezoelectric layer 1834.

The connectic layer 1836 may comprise various processing devices such as, for example, a processor, an application specific integrated circuit (ASIC), a controller, etc., support logic/circuitry, and interconnections between the various electronic devices to control the generation of acoustic waves, reception of the acoustic waves, etc. The connectic layer 1836 may also comprise acoustic matching and/or de-matching layers.

The transducer structure 1820 is similar to the transducer structure 1810, but there is no de-matching layer 1835.

In addition, various embodiments of the disclosure may incorporate thermally (heat) conductive materials in the core layer 114 so that the stressed-skin backing panel 210 is able to act as a heat sink. The thermally conductive material(s) may comprise, for example, metal particles, one or more graphites such as, for example, pyrolitic graphite, graphene, etc. Additionally, where an epoxy is used to adhere the skin layers 212, 1600, etc., to the core layer 114, the epoxy may be a thermally (heat) conductive epoxy.

Accordingly, it can be seen that the disclosure provides for a stressed-skin backing panel 210 for a transducer 204 of an ultrasound scanner probe 200, comprising a core layer 214 sandwiched by a first and second skin layers 212. The transducer 204 may comprise a front portion and a rear portion, where the front portion of the transducer 204 points to a direction of a target for the ultrasound scanner probe 200. The first skin layer 212a may be adjacent to the rear portion of the transducer 204. The first skin layer 212a may be directly adjacent to the transducer 204.

The core layer 214 may comprise epoxy material. The core layer 214 may comprise silicone based material. One or both of the first skin layer 212a or the second skin layer 212b may comprise tungsten carbide. The stressed-skin backing panel 210 may comprise heat conductive elements to conduct heat generated by the transducer 204. The heat conductive elements may comprise, for example, one or both of metal particles and graphite, where the graphite may comprise, for example, one or more of pyrolitic graphite, graphene, etc.

The stressed-skin backing panel 210 may comprise support pillars 320, 420, etc., coupled to one or both of the first skin layer 212a and the second skin layer 212b. The support pillars may comprise same material as one or both of the first skin layer 212a and the second skin layer 212b. One or both of the first skin layer 212a and the second skin layer 212b may be a unitary piece with the support pillars.

The first skin layer 212a and the second skin layer 212b may each comprise a first side facing the core layer 214, and one or both of the respective first sides may be a substantially non-planar surface.

A first percent of first acoustic waves in the core layer 214 reflected by the first skin layer 212a or the second skin layer 212b may be greater than a second percent of second acoustic waves outside the stressed-skin backing panel 210 reflected by the first skin layer 212a or the second skin layer 212b.

Epoxy material, which may be a conductive epoxy material, may be used to adhere the first skin layer 212a and/or the second skin layer 212b to the core layer 214. One or more peripheral surfaces of the core layer not covered by the first skin layer 212a and the second skin layer 212b may be covered by a third skin layer 900.

The disclosure may also provide for a stressed-skin backing panel 210 comprising a core layer 214 sandwiched by a first skin layer 212a and a second skin layer 212b, and support pillars 320, 420, etc., coupled to one or both of the first skin layer 212a and the second skin layer 212b. The core layer 214 may comprise one or both of epoxy material and silicone based material, where the transducer 204 may comprise a front portion and a rear portion. The front portion of the transducer 204 points to a direction of a target for the ultrasound scanner probe, and the first skin layer 212a is adjacent to the rear portion of the transducer 204.

One or both of the first skin layer 212a or the second skin layer 212b may comprise tungsten carbide. The stressed-skin backing panel 210 may comprise heat conductive elements to conduct heat generated by the transducer 204. The heat conductive elements may comprise one or both of metal particles and graphite, where the graphite may comprise, for example, one or more of pyrolitic graphite, graphene, etc. The first skin layer 212a and the second skin layer 212b may each comprise a first side facing the core layer 214, and one or both of the respective first sides may be a substantially non-planar surface.

As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations.

Accordingly, the present disclosure may be realized with various materials. While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What are claimed:

1. A stressed-skin backing panel for a transducer of an ultrasound scanner probe, comprising:
   a core layer comprising a top surface, a bottom surface, and peripheral surfaces extending between the top surface and the bottom surface;
   a first skin layer entirely covering the top surface of the core layer; and
   a second skin layer entirely covering the bottom surface of the core layer,
   wherein:
      the transducer comprises a front portion and a rear portion,
      the front portion of the transducer points to a direction of a target for the ultrasound scanner probe, and
      the first skin layer is adjacent to the rear portion of the transducer.

2. The stressed-skin backing panel of claim 1, wherein the first skin layer is directly adjacent to the transducer.

3. The stressed-skin backing panel of claim 1, wherein the core layer comprises epoxy material.

4. The stressed-skin backing panel of claim 1, wherein the core layer comprises silicone based material.

5. The stressed-skin backing panel of claim 1, wherein one or both of the first skin layer or the second skin layer comprises tungsten carbide.

6. The stressed-skin backing panel of claim 1, wherein the stressed-skin backing panel comprises at least one heat conductive element to conduct heat generated by the transducer.

7. The stressed-skin backing panel of claim 6, wherein the at least one heat conductive element comprises one or both of metal particles and graphite.

8. The stressed-skin backing panel of claim 1, comprising support pillars coupled to one or both of the first skin layer and the second skin layer.

9. The stressed-skin backing panel of claim 8, comprising support pillars wherein the support pillars comprise same material as one or both of the first skin layer and the second skin layer.

10. The stressed-skin backing panel of claim 8, wherein one or both of the first skin layer and the second skin layer is a unitary piece with the support pillars.

11. The stressed-skin backing panel of claim 1, wherein the first skin layer and the second skin layer each comprises a first side facing the core layer, and one or both of the respective first sides is a substantially non-planar surface.

12. The stressed-skin backing panel of claim 1, wherein a first percent of first acoustic waves in the core layer reflected by the first skin layer or the second skin layer is greater than a second percent of second acoustic waves outside the stressed-skin backing panel reflected by the first skin layer or the second skin layer.

13. The stressed-skin backing panel of claim 1, comprising epoxy material adhering the first skin layer and the second skin layer to the core layer.

14. The stressed-skin backing panel of claim 13, wherein the epoxy material is a conductive epoxy material.

15. The stressed-skin backing panel of claim 1, wherein one or more of the peripheral surfaces of the core layer not covered by the first skin layer and the second skin layer are covered by a third skin layer.

16. A stressed-skin backing panel, comprising:
   a core layer comprising a top surface and a bottom surface opposite the top surface;
   a first skin layer entirely covering the top surface of the core layer;
   a second skin layer entirely covering the bottom surface of the core layer; and
      support pillars coupled to one or both of the first skin layer and the second skin layer,
      wherein:
         the core layer comprises one or both of epoxy material and silicone based material,
         the transducer comprises a front portion and a rear portion,
         the front portion of the transducer points to a direction of a target for the ultrasound scanner probe, and
         the first skin layer is adjacent to the rear portion of the transducer.

17. The stressed-skin backing panel of claim 16, wherein one or both of the first skin layer or the second skin layer comprises tungsten carbide.

18. The stressed-skin backing panel of claim 16, wherein the stressed-skin backing panel comprises at least one heat conductive element to conduct heat generated by the transducer.

19. The stressed-skin backing panel of claim 18, wherein the at least one heat conductive element comprises one or both of metal particles and graphite.

20. The stressed-skin backing panel of claim 16, wherein the first skin layer and the second skin layer each comprises a first side facing the core layer, and one or both of the respective first sides is a substantially non-planar surface.

* * * * *